(12) United States Patent
Maloney

(10) Patent No.: US 6,889,363 B2
(45) Date of Patent: May 3, 2005

(54) INTERACTIVE MULTIMEDIA REPORT VIEWER

(75) Inventor: Krisellen Maloney, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 285 days.

(21) Appl. No.: 09/796,703

(22) Filed: Mar. 2, 2001

(65) Prior Publication Data

US 2002/0122057 A1 Sep. 5, 2002

(51) Int. Cl.[7] .................................................. G09G 5/00
(52) U.S. Cl. ...................... 715/765; 715/760; 715/762; 715/765; 715/781; 715/513; 715/744; 600/425; 600/427; 712/245
(58) Field of Search ................................ 345/760, 762, 345/781, 804, 788, 792, 799, 765, 424; 600/425, 427; 712/245; 711/166, 170; 707/513, 744

(56) References Cited

U.S. PATENT DOCUMENTS

| | | | |
|---|---|---|---|
| 4,567,515 A | 1/1986 | Schumacher | 382/305 |
| 5,452,416 A | 9/1995 | Hilton et al. | 715/783 |
| 5,600,574 A * | 2/1997 | Reitan | 702/185 |
| 5,712,995 A * | 1/1998 | Cohn | 345/792 |
| 5,803,914 A | 9/1998 | Ryals et al. | 600/407 |
| 5,954,650 A | 9/1999 | Saito et al. | 600/425 |
| 6,063,030 A | 5/2000 | Vara et al. | 600/437 |
| 6,081,267 A | 6/2000 | Stockham et al. | 715/788 |
| 6,115,626 A * | 9/2000 | Whayne et al. | 600/427 |
| 6,192,266 B1 * | 2/2001 | Dupree et al. | 600/427 |
| 6,272,469 B1 | 8/2001 | Koritzinsky et al. | 705/2 |
| 6,310,631 B1 * | 10/2001 | Cecco et al. | 345/792 |
| 6,342,907 B1 * | 1/2002 | Petty et al. | 345/762 |
| 6,401,138 B1 * | 6/2002 | Judge et al. | 709/328 |
| 6,476,833 B1 * | 11/2002 | Moshfeghi | 345/854 |
| 2001/0020243 A1 * | 9/2001 | Koppolu et al. | 707/513 |

* cited by examiner

Primary Examiner—Raymond J. Bayerl
Assistant Examiner—Cuong T. Thai
(74) Attorney, Agent, or Firm—Oblon, Spivak, McClelland, Maier & Neustadt, P.C.

(57) ABSTRACT

A method and system for controlling plural software components to communicate and share a single virtual or real monitor or display. By (1) sending messages to applications aware of data control messages and (2) killing and restarting non-aware applications, a consistent set of information (e.g., images and textual data) can be presented within a single user interface, even if the components used are not originally written with the intention of working together.

21 Claims, 20 Drawing Sheets

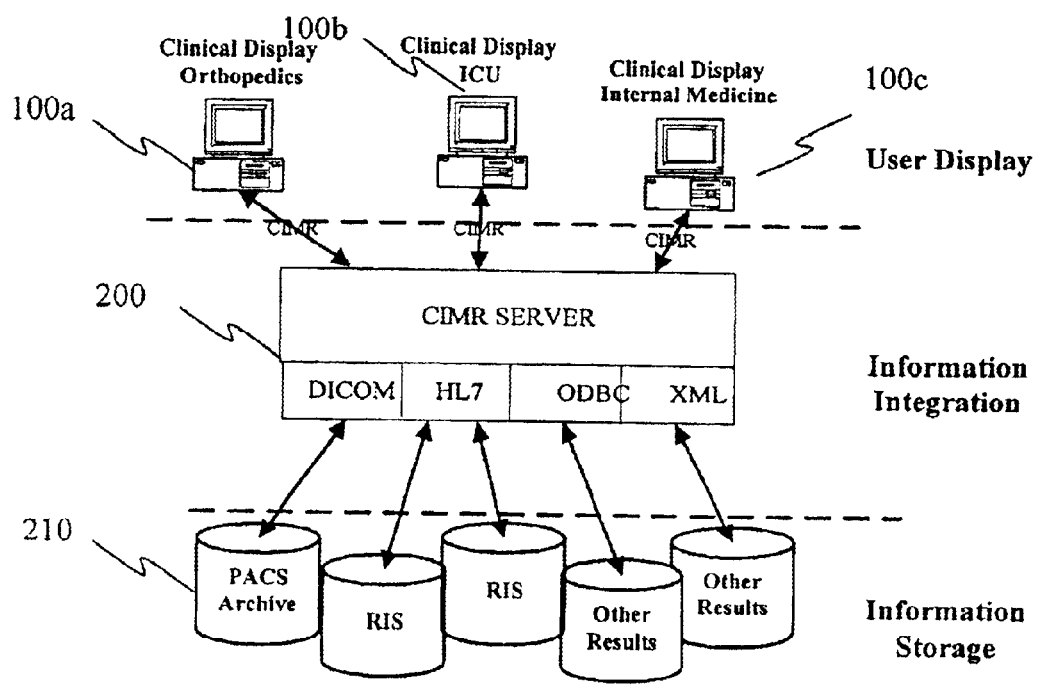
Figure 1A - Overview of CIMR Architecture

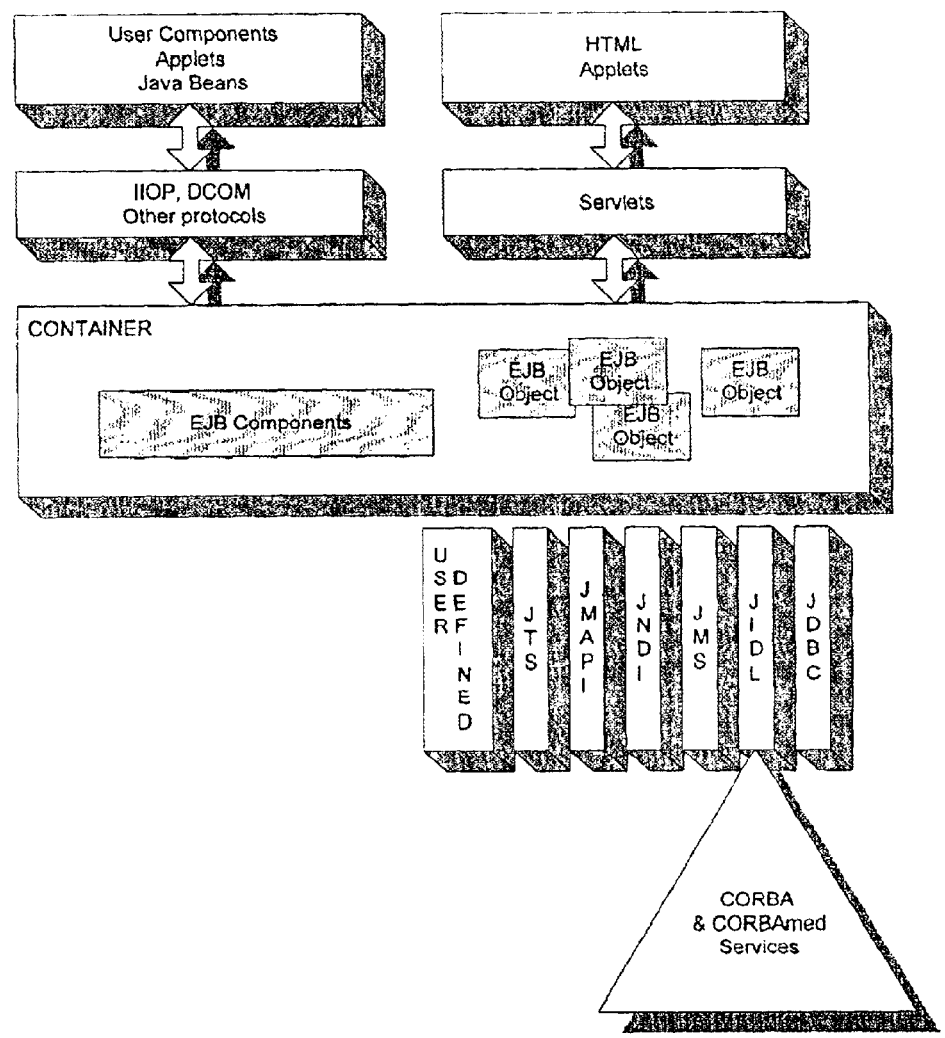
Figure 2 - Component technology based on Enterprise Java Beans

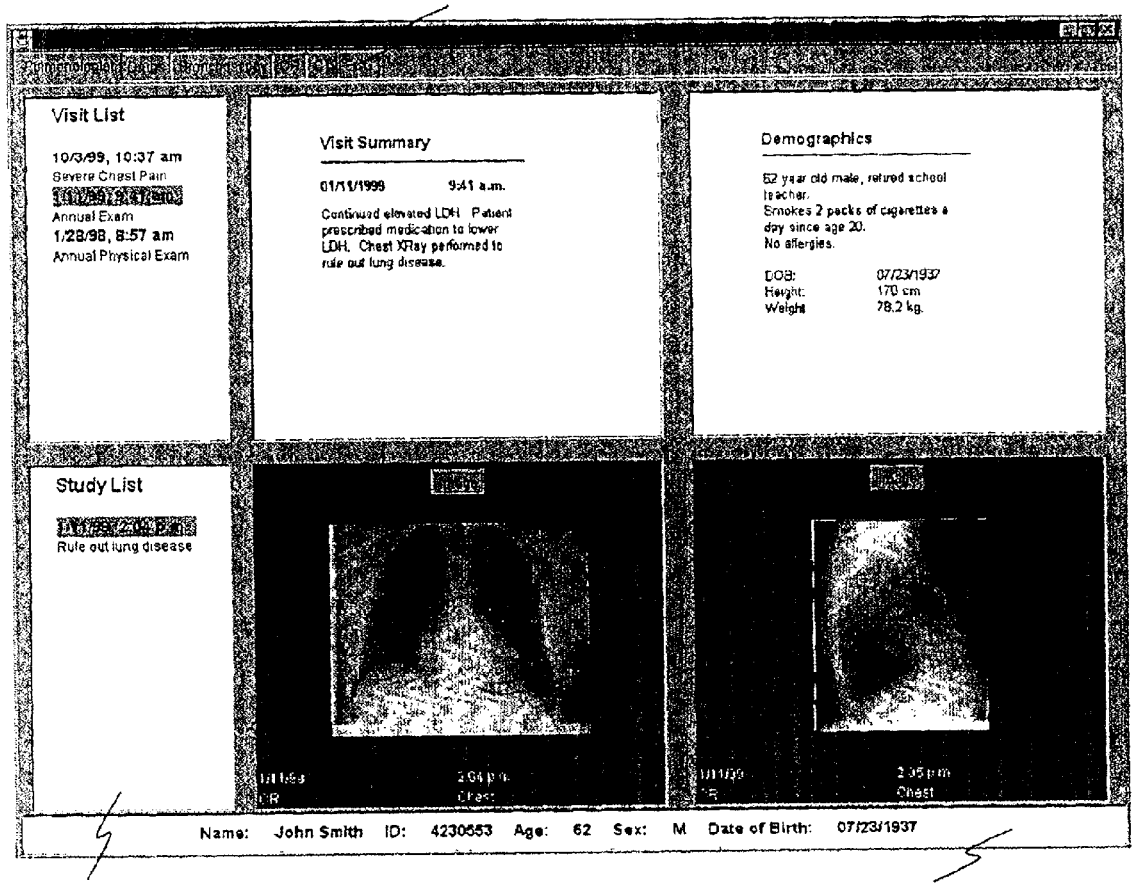
Figure 3 - Use of technology in radiology area

```
<!ELEMENT PATIENT (NAME,OTHERNAME,MRN,DEMOGRAPHICS,VISIT+)>
<!ELEMENT NAME (#PCDATA)>
<!ELEMENT OTHERNAME (#PCDATA)>
<!ELEMENT MRN (#PCDATA)>
<!ELEMENT DEMOGRAPHICS (OCCUPATION,CONFIDENTIALITY,DOB,SIZE,
    WEIGHT,AGE,ADDRESS,COUNTRYOFRESIDENCE,TELEPHONENUMBERS,
    USERDEFINEDCOMMENTS,MEDICALALERTS,CONTRASTALLERGIES,
    SMOKINGSTATUS,ADDITIONALPATIENTHISTORY,PREGNANCYSTATUS,
    SPECIALNEEDS,PATIENTSTATE,SEX,DEMOG,HIS)>
<!ELEMENT OCCUPATION (#PCDATA)>
<!ELEMENT CONFIDENTIALITY (#PCDATA)>
<!ELEMENT DOB (#PCDATA)>
<!ELEMENT SIZE (#PCDATA)>
<!ELEMENT WEIGHT (#PCDATA)>
<!ELEMENT AGE (#PCDATA)>
<!ELEMENT ADDRESS (#PCDATA)>
<!ELEMENT COUNTRYOFRESIDENCE (#PCDATA)>
<!ELEMENT TELEPHONENUMBERS (#PCDATA)>
<!ELEMENT USERDEFINEDCOMMENTS (#PCDATA)>
<!ELEMENT MEDICALALERTS (#PCDATA)>
<!ELEMENT CONTRASTALLERGIES (#PCDATA)>
<!ELEMENT SMOKINGSTATUS (#PCDATA)>
<!ELEMENT ADDITIONALPATIENTHISTORY (#PCDATA)>
<!ELEMENT PREGNANCYSTATUS (#PCDATA)>
<!ELEMENT SPECIALNEEDS EMPTY>
<!ELEMENT SEX (#PCDATA)>
<!ELEMENT DEMOG (#PCDATA)>
<!ELEMENT HIS (#PCDATA)>
<!ELEMENT VISIT (VISITID,VISITSTATUS,CURRENTLOCATION,
    INSTITUTIONRESIDENCE,REFERRINGPHYSICIAN,REFERRINGPHYSICIANPHONE,
    REASONFORVISIT,ADMISSIONROUTE,VISITDATE,VISITTIME,VISITSUMMARY?,
    RIS?,FINDINGS?,DRUGS?,ECGSTUDY*,CRSTUDY*,DERMSTUDY*,FBSSTUDY*,
    ECSTUDY*)>
<!ELEMENT VISITID (#PCDATA)>
<!ELEMENT VISITSTATUS (#PCDATA)>
<!ELEMENT CURRENTLOCATION (#PCDATA)>
<!ELEMENT INSTITUTIONRESIDENCE EMPTY>
<!ELEMENT REFERRINGPHYSICIAN (#PCDATA)>
<!ELEMENT REFERRINGPHYSICIANPHONE (#PCDATA)>
<!ELEMENT REASONFORVISIT (#PCDATA)>
<!ELEMENT ADMISSIONROUTE (#PCDATA)>
<!ELEMENT VISITDATE (#PCDATA)>
```

*FIG. 5A*

```
<!ELEMENT VISITTIME (#PCDATA)>
<!ELEMENT VISITSUMMARY (#PCDATA)>
<!ELEMENT RIS (#PCDATA)>
<!ELEMENT FINDINGS (#PCDATA)>
<!ELEMENT DRUGS (#PCDATA)>
<!ELEMENT ECGSTUDY (REASONFORSTUDY,STUDYINSTANCEUID,STUDYDATE,
      STUDYTIME,DESCRIPTION,BODYPART,ACCESSIONNUMBER,
      REPORTSERIES,ADDITIONALHISTORY,ICON,ORIGINALREPORT,SERIES)>
<!ELEMENT REASONFORSTUDY (#PCDATA)>
<!ELEMENT STUDYINSTANCEUID (#PCDATA)>
<!ELEMENT STUDYDATE (#PCDATA)>
<!ELEMENT STUDYTIME (#PCDATA)>
<!ELEMENT DESCRIPTION (#PCDATA)>
<!ELEMENT BODYPART (#PCDATA)>
<!ELEMENT ACCESSIONNUMBER (#PCDATA)>
<!ELEMENT REPORTSERIES (ORIGINALREPORT)>
<!ELEMENT ADDITIONALHISTORY (#PCDATA)>
<!ELEMENT ICON (#PCDATA)>
<!ELEMENT ORIGINALREPORT (#PCDATA)>
<!ELEMENT SERIES (SERIESINSTANCEUID,IMAGE+)>
<!ELEMENT SERIESINSTANCEUID (#PCDATA)>
<!ELEMENT IMAGE (IMAGEICON,IMAGEINSTANCEUID,IMAGETYPE,IMAGEDATE,
      IMAGETIME)>
<!ELEMENT IMAGEICON (#PCDATA)>
<!ELEMENT IMAGEINSTANCEUID (#PCDATA)>
<!ELEMENT IMAGETYPE (#PCDATA)>
<!ELEMENT IMAGEDATE (#PCDATA)>
<!ELEMENT IMAGETIME (#PCDATA)>
<!ELEMENT ECSTUDY (REASONFORSTUDY,STUDYINSTANCEUID,STUDYDATE,
      STUDYTIME,DESCRIPTION,BODYPART,ACCESSIONNUMBER,
      REPORTSERIES,ADDITIONALHISTORY,ICON,SERIES)>
<!ELEMENT CRSTUDY (REASONFORSTUDY,STUDYINSTANCEUID,STUDYDATE,
      STUDYTIME,DESCRIPTION,BODYPART,ACCESSIONNUMBER,
      REPORTSERIES,ADDITIONALHISTORY,ICON,SERIES)>
<!ELEMENT DERMSTUDY (REASONFORSTUDY,STUDYINSTANCEUID,STUDYDATE,
      STUDYTIME,DESCRIPTION,BODYPART,ACCESSIONNUMBER,
      REPORTSERIES,ADDITIONALHISTORY,ICON,SERIES)>
<!ELEMENT FBSSTUDY (REASONFORSTUDY,STUDYINSTANCEUID,STUDYDATE,
      STUDYTIME,DESCRIPTION,BODYPART,ACCESSIONNUMBER,
      REPORTSERIES,ADDITIONALHISTORY,ICON,SERIES)>
```

FIG. 5B

```
<Component>
    <Name>StudyList</Name>
    <ViewProperties>
        <MinWidth>180</MinWidth>
        <MinHeight>320</MinHeight>
        <BGColor>Black</BGColor>
    </ViewProperties>
    <StatusProperties>
        <Visit>0</Visit>
        <study>0</study>
        <Active>1</Active>
        <Follow>Visit</Follow>
    </StatusProperties>
    <Implementation>
        <BuilderClass>
            <BuilderType>JavaComponentBuilder</BuilderType>
            <Path>FULLPATH\Study.class</Path>
            <Argument>Document</Argument>
        </BuilderClass>
        <StudiesDisplayed>
            <Name>CRStudy</Name>
            <Name>DermStudy</Name>
        </StudiesDisplayed>
    </Implementation>
</Component>
```

*FIG. 7*

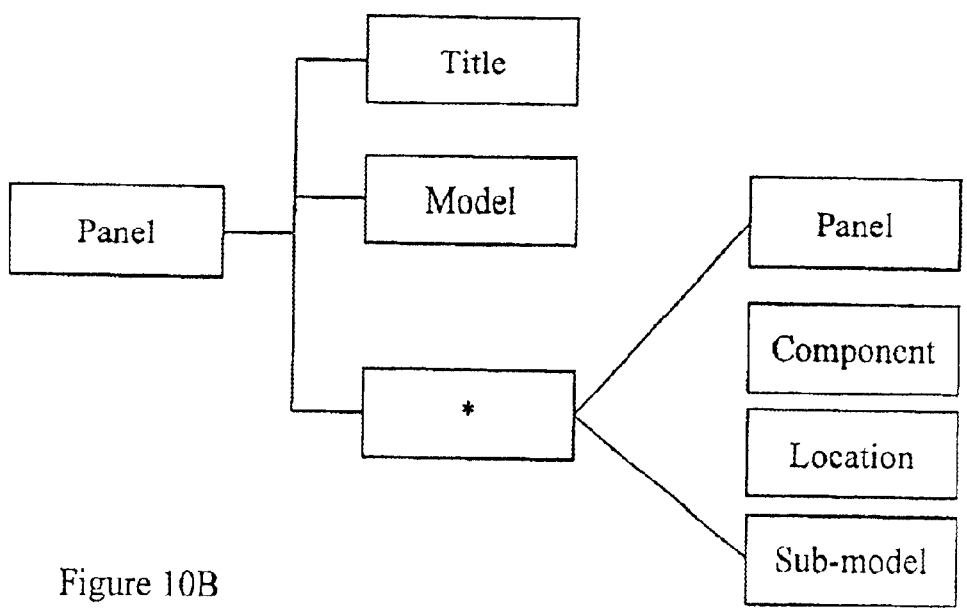
Figure 10B
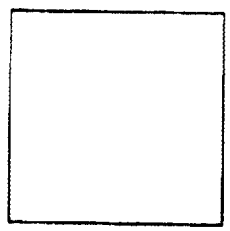
Figure 9A
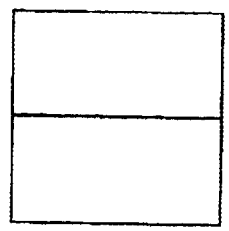
Figure 9B
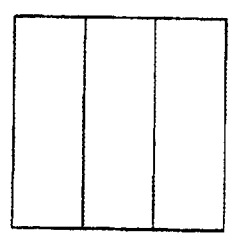
Figure 9C
| 1 | 3 |
|---|---|
| 2 | 4 |
Figure 9D

```
<Layout>
    <Title>CR</Title>
    <Description>PACS Screen</Description>
    <Panel>
        <Model>VHalf</Model>
        <Panel>
            <Model>HHalf</Model>
            <Location>West</Location>
            <Panel>
                <Model>Full</Model>
                <Location>North</Location>
                <Component>
                information about Component1
                </Component>
            </Panel>
            <Panel>
                <Model>Full</Model>
                <Location>South</Location>
                <Component>
                information about Component2
                </Component>
            </Panel>
        </Panel>
    <Panel>
        <Model>HHalf</Model>
        <Location>East</Location>
            <Panel>
                <Model>Full</Model>
                <Location>North</Location>
                <Component>
                    information about Component3
                </Component>
            </Panel>
            <Panel>
                <Model>Full</Model>
                <Location>South</Location>
                <Component>
                    information about Component4
                </Component>
            </Panel>
        </Panel>
    </Panel>
</Layout>
```

Figure 10A

```
<!ELEMENT High (LayoutList, Status )>
<!ELEMENT LayoutList (Layout+ )>
<!ELEMENT Layout ( ( )* , Title , Description , Panel , Panel )>
<!ELEMENT Panel (Title , Model , (Panel | Component | Location | Submodel )* )>
<!ELEMENT Title (#PCDATA )>
<!ELEMENT Model (#PCDATA )>
<!ELEMENT Location (#PCDATA )>
<!ELEMENT Component (Name, ViewProperties, StatusProperties, Implementation )>
<!ELEMENT Name (#PCDATA )>
<!ELEMENT Width (#PCDATA )>
<!ELEMENT Height (#PCDATA )>
<!ELEMENT BuilderClass (BuilderType , Path , Argument )>
<!ELEMENT BuilderType (#PCDATA )>
<!ELEMENT Path (#PCDATA )>
<!ELEMENT Argument (#PCDATA )>
<!ELEMENT ModalityList (Name )>
<!ELEMENT Visit (#PCDATA )>
<!ATTLIST Visit number (0 ) #IMPLIED >
<!ELEMENT Study (#PCDATA )>
<!ATTLIST Study number (0 ) #IMPLIED >
<!ELEMENT Series (#PCDATA )>
<!ATTLIST Series number (0 ) #IMPLIED >
<!ELEMENT Image (#PCDATA )>
<!ATTLIST Image number (0 ) #IMPLIED >
<!ELEMENT Active (#PCDATA )>
<!ELEMENT MostRecent (#PCDATA )>
<!ELEMENT Clickable (#PCDATA )>
<!ELEMENT Reportable (#PCDATA )>
<!ELEMENT Description (#PCDATA )>
<!ELEMENT Submodel (#PCDATA )>
<!ELEMENT Color (#PCDATA )>
<!ELEMENT Follow (#PCDATA )>
<!ELEMENT TagToDisplay (#PCDATA )>
<!ELEMENT Status (Visit )>
<!ELEMENT CRStudy (Series )>
<!ATTLIST CRStudy number CDATA #REQUIRED >
<!ELEMENT CTStudy (Series )>
<!ATTLIST CTStudy number CDATA #REQUIRED >
<!ELEMENT MRStudy (Series )>
<!ATTLIST MRStudy number CDATA #REQUIRED >
<!ELEMENT ECGStudy (Series )>
<!ATTLIST ECGStudy number CDATA #REQUIRED >
<!ELEMENT ViewProperties (Height , Color , Width )>
<!ELEMENT StatusProperties (Visit, Study, Series, Image, Active,
            Follow, MostRecent )>
<!ELEMENT Implementation (BuilderClass , BuilderType , Path , Argument , ModalityList ,
            Clickable , Reportable , TagToDisplay )>
```

Figure 12

INTERACTIVE MULTIMEDIA REPORT VIEWER

BACKGROUND OF THE INVENTION

1. Field of the Invention

The present invention is directed to a method and system for coordinating multiple software components to communicate and share a portion of a computer monitor or display.

2. Discussion of the Background

Numerous program display control systems have been used to coordinate the display of some number of programs on a single (virtual or real) display/monitor. In the X Windows environment, such a control system is called a windows manager. Examples of known windows managers include: FVWM, FVWM95, TWM/VTWM, MWM, CTWM, OLWM/OLVWM, wm2/wmx, AfterStep, AmiWM, Enlightenment, WindowMaker, SCWM, IceWM, Sawfish, and Blackbox. Using configuration files for the applications run under the X Windows window managers, certain windowing parameters (e.g., windows locations and colors) can be set at application start-up time.

In X Windows, libraries of various re-usable components have been built to standardize the look and feel of various components within a graphical user interface. Such libraries include OpenLook and Motif and implement "widgets" having a variety of functions (e.g., buttons and menus).

A consortium of participants in the health care industry have combined to form the Clinical Context Object Workgroup (CCOW), which, according to its 1998 White Paper, "publishes standards for the visual integration of cooperative interaction among independently authored healthcare applications at the point of use." As further stated therein "Version 1 of the standard [ratified in April 1999], the Patient Link, supports synchronizing the applications for a selected patient. When the user of an application changes the selected patient, the other applications on the workstation follow the change. The cooperation frees the user from the tedium of repeating the action in more than one application." Subsequently versions 1.1 and 1.2 were ratified in January and May, 2000, respectively.

SUMMARY OF THE INVENTION

The present invention is directed to a method and system for displaying synchronized data across plural independently developed components. In one embodiment of the present invention, the access to the data is read-only; however, in an alternate embodiment, at least a portion of the data is writeable by one of the components.

This and other objects of the present invention are addressed by providing a series of components that can be instantiated with a series of run-time display parameters. In one embodiment thereof, at least one component can either (1) signal other components of a change in data of common interest or (2) kill the other components and restart them with new run-time parameters such that the display areas of the components form a single consistent display.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a component diagram of exemplary applet-based implementation techniques for implementing the displays of FIG. 1;

FIG. 3 is an exemplary user interface created for an exemplary medical application in which patient textual and graphic information is coordinated between the several components;

FIGS. 5A and 5B are an exemplary patient description grammar representing relationships between various client information;

FIG. 7 is an exemplary set of properties conforming to the entity-relationship diagram of FIG. 6;

FIGS. 9A–9D are various panels for use in laying out information;

FIG. 10A is an exemplary XML-based hierarchical combination of components for forming a four-panel window from separate horizontal and vertical panels;

FIG. 10B is a graphical description of a grammar for defining hierarchical panels;

FIG. 12 is an exemplary component layout grammar representing relationships between various layout components within the system;

DETAILED DESCRIPTION OF THE PREFERRED EMBODIMENT

Figure 1B:
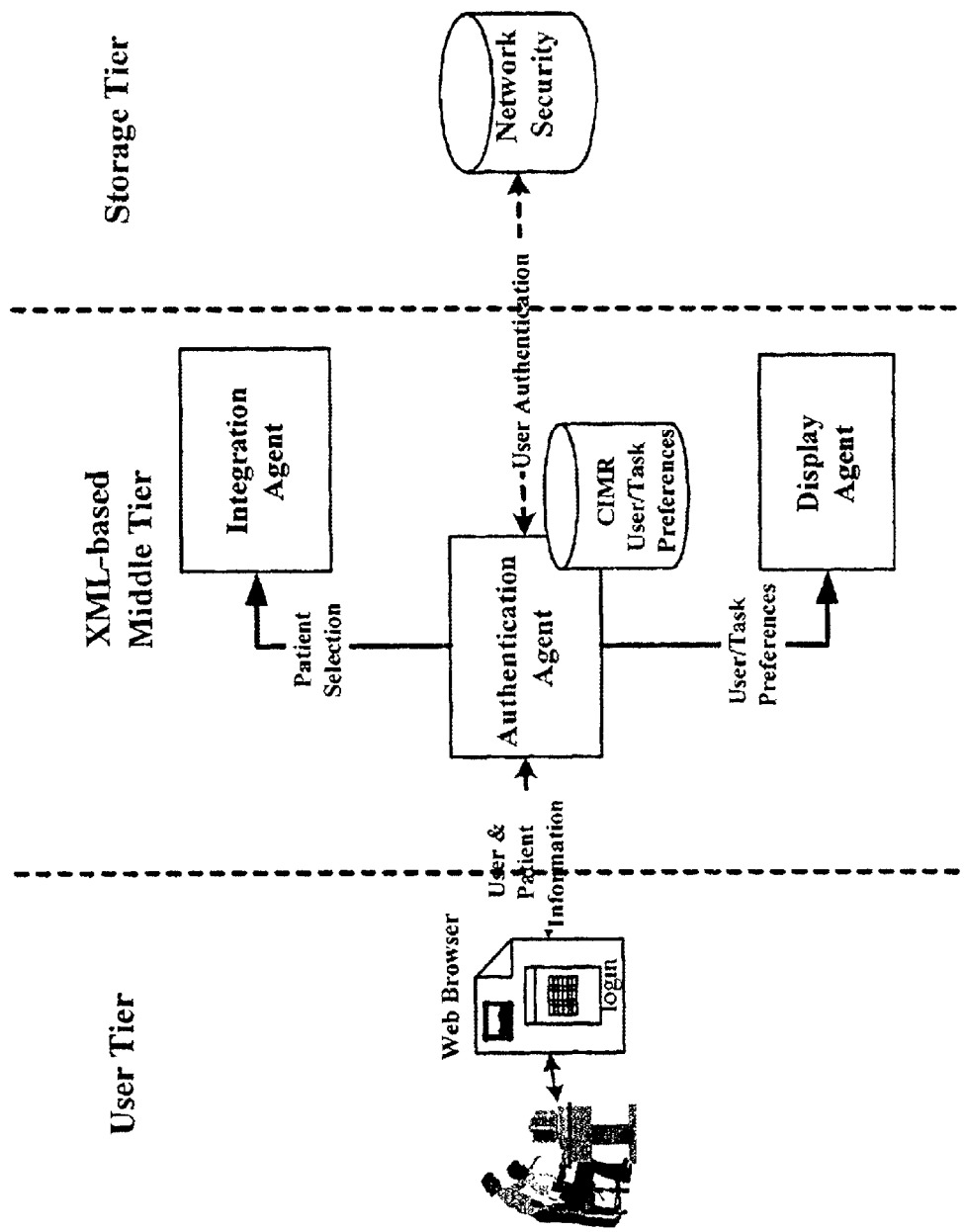
FIG. 1 is a block diagram of a network of computers sharing a common information storage system that is accessed via information integration tools and/or interfaces such that domain-specific interfaces can be developed more rapidly and consistently.

Referring now to the drawings, wherein like reference numerals designate identical or corresponding parts throughout the several views, FIG. 1A is a schematic illustration of a network of computers 100a, 100b, and 100c that share a common information storage system 210 that is accessed via information integration tools and/or application programming interfaces (APIs) 200. Domain-specific user interfaces (DSUIs) can be developed using the APIs 200. The exemplary DSUIs of computers 100a, 100b, and 100c are (a) an orthopedics display, (b) an intensive care unit (ICU) display, and (c) an internal medicine display, respectively. Other DSUIs are also possible, in both the medical domain as well as other domains, where the displays of multiple components need to be kept in synchronization, either (1) in their independent windows or (2) within the bounds of a single integrated window.

In complex systems, such as patient information systems acting as DSUIs, data is generated by many sources and stored within the information storage system 210 in a variety of formats. For example, radiological data may be stored in a first database as images and other patient information (e.g., EKG traces or pathological results) information may stored in a second database as at least one of images and text. Demographic information may be stored in the same or a different database and is associated with the other patient information. In addition, read and write access to the data of the information storage system 210 is preferable for at least one component. Data preferably is also communicated in a variety of formats (e.g., DICOM, HL7), wherein representations facilitating use by the components directly are the most preferable. The eXtensible Markup Language (XML) provides a simple and robust extendible standard for data representation and exchange. Since XML file are distributed with their own descriptions, XML creates an integrated information object. Thus, XML is (1) structured, (2) extensible and (3) provides validation. XML provides a structure to store and identify information (e.g., patient information in a medical context or suspect/criminal information in a criminal context). The information is structured hierarchically much like objects within the software design. The XML structure can be extended as new information becomes available. XML provides mechanisms to ensure data validity and can be searched directly using query language tools such as XMLSQL.

FIG. 1B is a data flow model that illustrates the information flow to people or agents (e.g., using a Web browser or other GUI interface). That model includes several high-level steps (each which may be implemented with additional sub-steps or optional steps) including: (1) login, (2) object selection (e.g., patient selection), (3) information display, and (4) user preference management.

A user's login information can be validated in any manner (e.g., NT authentication or CORBA Security Services). Generally, though, an Authentication Agent acts as a gatekeeper between users and data. In one embodiment, the authentication process allows a user to access user preferences for those features of a DSUI that are customizable. More importantly, though, once authenticated, the user is given the type and scope of access that corresponds to the access rights authorized by the system. Some users may have read-only access, while others have read and write access. Moreover, not all users will be able to see all the data of a system. For example, while hospital administrators may be able to see billing information about a patient's visit, the actual radiographic or diagnostic information is not available. Thus, in one embodiment, the Authentication Agent acts as a continuous middleman during the process of selecting patient records.

Such selection can be through a number of mechanisms (e.g., by number, by location). In a medical environment, the Authentication Agent sends the patient record selection information to an Integration Agent. This selection information will be used to build patient information for display and return to the user. However, since a user may have customized part of a display interface, a Display Agent also accesses that customization information to properly format the results to be displayed. As discussed in greater detail below, users of a standard interface may rearrange that interface in order to suit the user's preference. One such rearrangement includes the internationalization of the interface to accommodate languages read right-to-left instead of left-to-right.

Figure 1C:
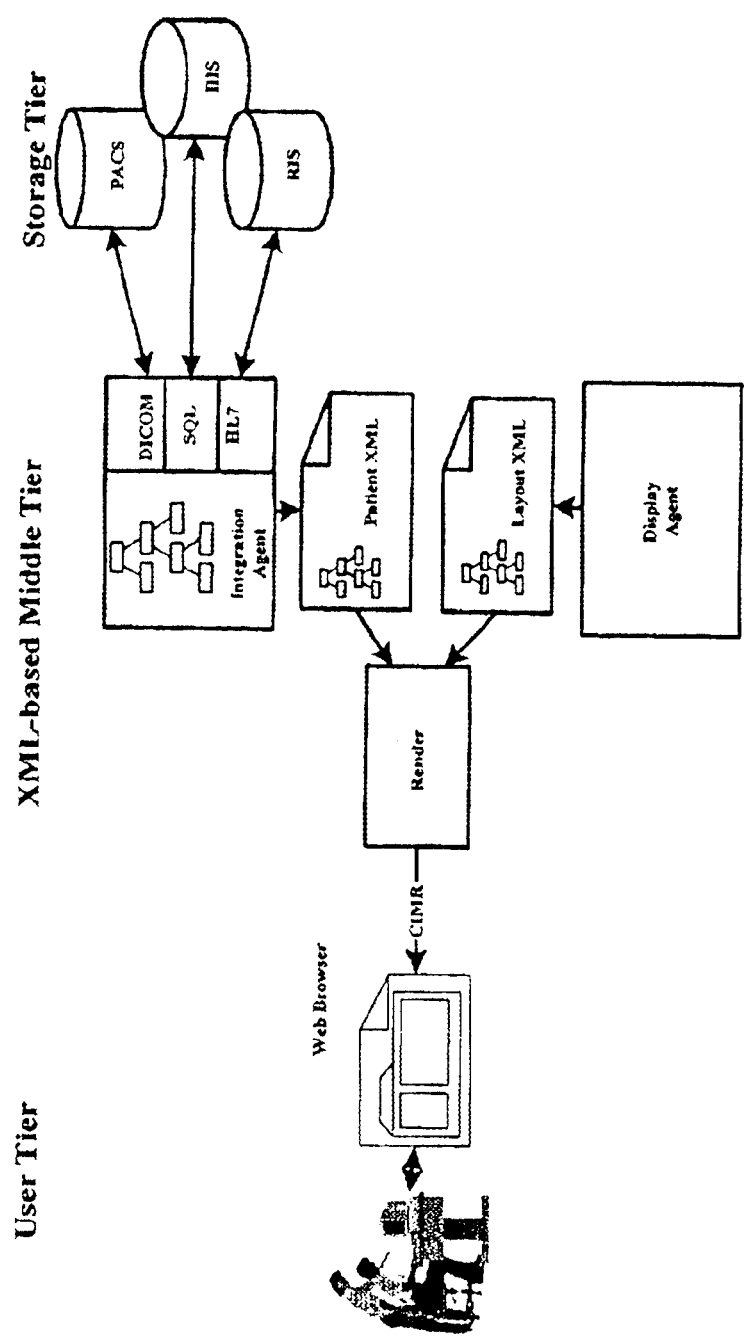

FIG. 1C further illustrates how data is combined from several locations to create the finally rendered layout with the requested data. Generally, the Integration Agent accesses information from at least one source to build a patient description data block (preferably using XML). The interfaces for accessing each data source in its own native standard may be implemented as separate modules or within a single module, but preferably such implementation choices are hidden behind a database abstraction that also hides a physical location of the data. In one embodiment, this agent utilizes known horizontal component services (e.g., Patient Identification Services provided by CORBAMed). In another embodiment, a Repository or other centralized data store (including either or both of database- and file-based systems) is utilized.

The Display Agent accesses a local store of Layout structures (e.g., in an XML-format). These structures are developed by the layout editor (see FIG. 11) and stored in a portion of the database that corresponds to display constraints.

Finally, the data and layout are combined (i.e., rendered) by the Rendering component. This process combines the retrieved Patient information with the layout information. The Rendering component may also utilize context information about the information to be displayed (e.g., a patient's records) before forwarding the complete report to the user.

According to a preferred embodiment, the single integrated window is used as a component-based application within a web-based architecture. Generally, the component architecture allows system developers to create reusable, portable software components that are designed for a specific purpose. Preferably, those components are small, easy to understand and maintain, and fulfill a narrow function within a larger application. By encapsulating functionality in software components, the applications developer can then have a library of common components that can be used to build up applications rapidly. By keeping the functionality of components narrow, individual components may be used (or reused) by many applications. The resulting componentware can be developed more rapidly and can accommodate portability.

To facilitate reuse, a series of standard interfaces and component technologies are preferably used. There are many technologies available that abstract the details of the system implementation away from the development of software. Using the web paradigm, systems communicate regardless of the platform O/S (e.g., Windows 9X, Mac, UNIX, Windows NT). The web server hides the details of the implementation from the client. Servers can utilize technologies such as Common Gateway Interface (CGI) and Active Server Pages (ASP) to represent results in HTML format. However, HTML lacks the richness and self-descriptive properties of XML. In addition, server-side components (e.g., CGI scripts and programs) are often machine-dependent. Thus, although CGI helps to move towards platform independence, it has portability disadvantages. The use of Java virtual machines and bytecodes increases portability for component-based software systems in an environment of multiple operating systems and diverse development languages. In addition to using lower-level components as building blocks of systems, higher level components (or complete applications) manage the presentation and integration of the lower-level components.

Cross platform portability is enhanced by a variety of complementary technologies which include Java, Enterprise Java Beans (EJB) and CORBA. Moreover, other object models (e.g., DCOM) can also be used, as long as the operation of the components is separated from the function of the context framework. The relationship of some of those technologies is illustrated in FIG. 2. CORBA provides mechanisms to distribute components among disparate systems. In addition it provides services (e.g., security, naming, transaction processing) to further insulate applications from the details of components' implementation. EJB goes one step further than CORBA by providing a container that acts as a Web Operating System. The container maintains the details of an implementation, providing an additional layer of abstraction for applications.

By using the component technologies described above, it is possible to create various DSUIs that act as applets. (Non-applet based technologies are also possible, as described in greater detail below with reference to FIGS. 13–17.) One such DSUI is the pulmonologist interface illustrated in FIG. 3. That DSUI provides a variety of display controls, including six tabs 250, six panels 260, and an information status bar 270. Each of the six tabs 250 corresponds to a page selection (much like selecting tabbed index cards from a box). Each of the six panels 260 is kept in synchronization with the information contained in the status bar 270, and vice versa. Thus, if the user of the pulmonologist interface changes to a different user using one display control (e.g., by selecting a new visit from a visit list (e.g., implemented as any one of a textual list, a drop-down box, a scrolling list and a set of radio buttons)), all the remaining display controls are controlled to change accordingly (e.g., using messaging as described below).

Figure 4:
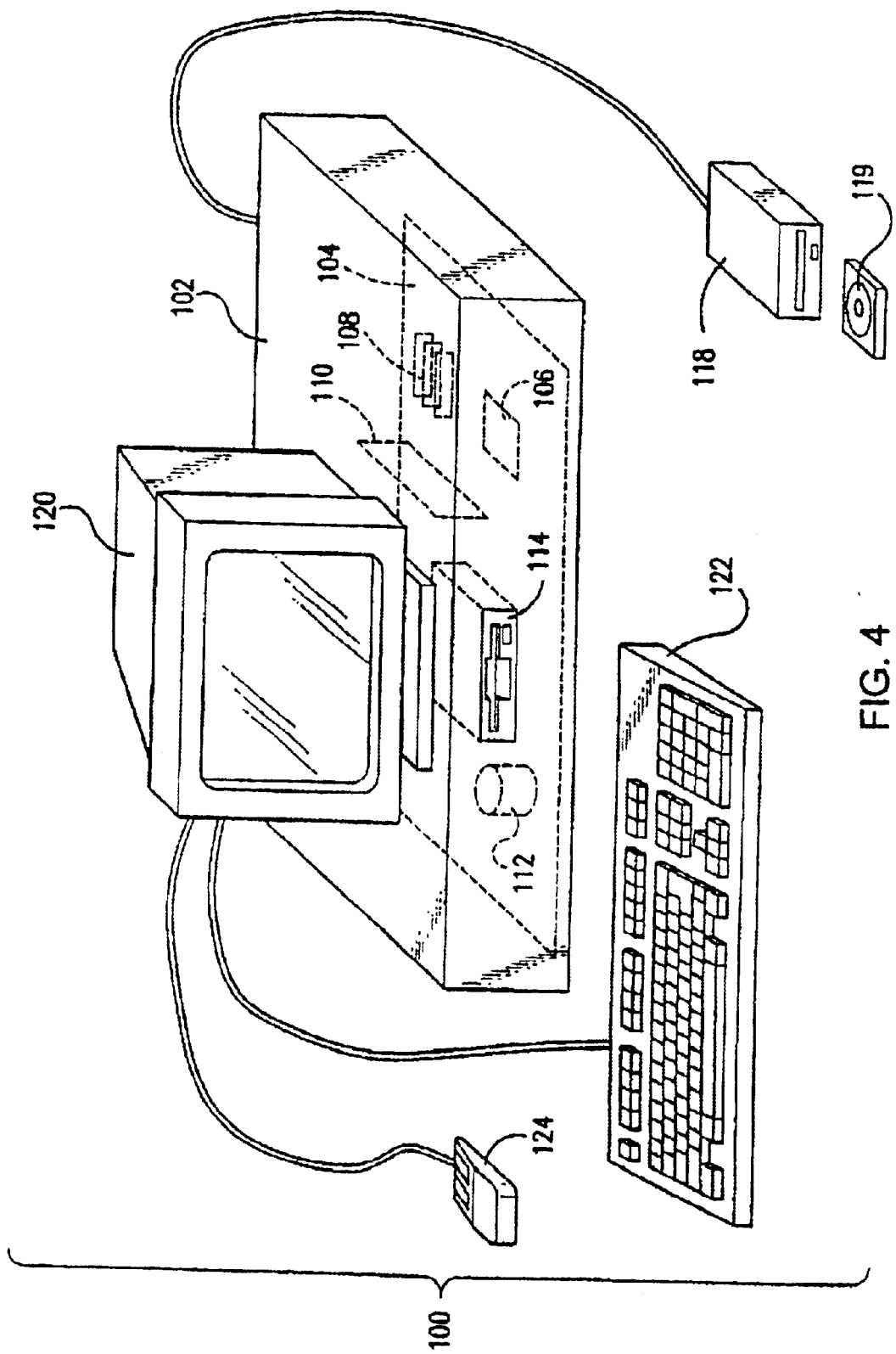
FIG. 4 is a schematic illustration of a computer system for use as any one of the user displays of FIG. 1.

FIG. 4 is a schematic illustration of a computer system for providing coordinated image and data display. A computer 100 implements the method of the present invention, wherein the computer housing 102 houses a motherboard 104 which contains a CPU 106; memory 108 (e.g., DRAM, ROM, EPROM, EEPROM, SRAM, SDRAM, and Flash RAM), and other optional special purpose logic devices (e.g., ASICs) or configurable logic devices (e.g., GAL and reprogrammable FPGA). The computer 100 also includes plural input devices, (e.g., a keyboard 122 and mouse 124), and a display card 110 for controlling monitor 120. In addition, the computer system 100 further includes a floppy disk drive 114; other removable media devices (e.g., compact disc 119, tape, and removable magneto-optical media (not shown)); and a hard disk 112, or other fixed, high density media drives, connected using an appropriate device bus (e.g., a SCSI bus, an Enhanced IDE bus, or a Ultra DMA bus). Also connected to the same device bus or another device bus, the computer 100 may additionally include a compact disc reader 118, a compact disc reader/writer unit (not shown) or a compact disc jukebox (not shown). Although compact disc 119 is shown in a CD caddy, the compact disc 119 can be inserted directly into CD-ROM drives which do not require caddies. In addition, a printer (not shown) also provides printed listings of reports from the coordinated displays.

As stated above, the system includes at least one computer readable medium. Examples of computer readable media are compact discs 119, hard disks 112, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer 100 and for enabling the computer 100 to interact with a human user. Such software may include, but is not limited to, device drivers, operating systems and user applications, such as development tools. Such computer readable media further includes the computer program product of the present invention for providing coordinated control of display controls or components. As described herein, the computer code devices of the present invention can be any interpreted or executable code mechanism, including but not limited to scripts (including CGI scripts), interpreters, dynamic link libraries, Java classes, Java beans, Active X controls, CCOW-compliant controls and complete executable programs. Moreover, the computer code devices can be downloaded dynamically from a computer network adapter acting as an equivalent to a computer readable medium. In addition, the number of components that are implemented by a single computer code device, or the number of computer code devices that are required to make up a single component can vary from component-to-component.

By providing a hierarchical set of components, components can be divided by functionality. An exemplary division of labor includes (1) components to access and store information in existing hospital systems, (2) components to configure information using XML meta-structures, and (3) components to handle data presentations (e.g., graphing components, image components for displaying images in a variety of formats (e.g., TIFF, GIF, JPEG, bitmap)).

Such a set of components also allows security to be addressed separately. At least two general approaches are possible for Security. First, the security features implemented within components themselves can be used. Basically, this means that security is not an issue of the overall system, but rather of the components utilized by the system. As the security capabilities of components evolve, the system automatically incorporate these components.

The second approach utilizes a "security component" or uses one of the horizontal services provided by CORBA. Such a component can take responsibility for validating user access and can mediate communications by components to ensure that security policies are enforced. This approach provides a greater level of security but requires increased cooperation from other components. Use of such a security component as well as CORBA services thus needs to be standardized, thereby reducing the ability to utilize 3rd party components.

A hierarchical component organization also localizes specialized access and display programming. When no access standard is in place, access to the proprietary information can be isolated in a manageable location. XML provides mechanisms (e.g., CSS, XSLT, XSL) to render information for display. Those mechanisms allow the same information to be associated with different display characteristics depending on the user and the task. For example, a patient's age may place him/her in a low risk group for one characteristic or disease but in a high risk group for another characteristic or disease.

By accessing data via named Element Tags in an XML-based Document Object Model, components can be configured with an additional level of indirection. The name of the tag (i.e., the programming variable) that contains the information needed is known in advance. This allows the implementation of a generalized wrapper component that can be used to allow existing software (e.g., an Algotec MediSurf Viewer) to be integrated with the Patient Context Component. For example, if it is necessary to invoke MediSurf with the StudyInstanceUID such as:

http://medisurf/start?study_display
 (1.2234.4434.3455.345654)

an external specification (within the layoutXML) is created to send the contents of the StudyInstanceUID to the named application. Using the same method, other software can be wrapped as long as the parameters to the software are included in a Patient description language (e.g., an XML-based DTD). Because of this additional level of indirection the software can send any instance of a tagged parameter to the software component. A component can be programmed to send the most recent, the most recent previous or any other instance of the tagged element to the external component.

Components within the system of the present invention are assumed to be "wellbehaved." Accordingly, such components are assumed to enforce data integrity (e.g., concurrency control), utilize authentication (e.g., user-level authentication for patient and exam information), and co-operate with dissimilar component types (CORBA, EJB and DCOM). For components that are not considered to be well behaved or are found to not enforce assumptions of the system, those components are isolated from the other components to prevent data corruption, etc.

Returning to FIG. 3, domain-specific information (e.g., patient information), layout information and context information are combined to form an exemplary DSUI. An exemplary structure for patient description language is illustrated in FIGS. 5A and 5B. (By using XML and DOM to hold the patient information, named tags can be associated with components).

Using the DSUI of FIG. 3, the tabs 250 represent six different information views: (1) Pulmonologist: a view that provides summary information, (2) Drugs: a listing of the patient's medications, (3) Bronchoscopy: views of visible light images of the bronchus, (4) CR: views of CR images, (5) CT: views of CT images, and (6) ECG: views of scanned ECG images. Preferably, each of those tabs is at least partially configurable (e.g., configuring the name tab, the order of the views, and the contents of the view).

The context of a DSUI provides a consistent view of the information among all of the tabbed pages as the end-user interacts with the information. In a medical environment, a context may include variables such as 'ActiveVisit', 'Active CRStudy', 'Active Series', etc. A component can be configured to track (or remain consistent with) a Context Variable. Utilizing the example of FIG. 3, information related to a visit on Jan. 11, 1999 is displayed. The first view in the layout, the Pulmonologist view, includes the visit list component, the visit summary component, the study list component and two image display components. Each of those components displays information related to the Jan. 11, 1999 visit. In addition, there is a demographic component that displays information in a status bar that is related to the patient. That component contains information that does not change with the visit. Additional views (not shown), for example the CR view, may also contain information relevant to the Jan. 11, 1999 visit.

When a user subsequently selects the Oct. 3, 1999 visit from the visit list component of the Pulmonologist view, that view changes so that the components that relate to the visit also change (e.g., the visit summary component provides information about the Oct. 3, 1999 visit, the study list component displays a list of studies for the Oct. 3, 1999 visit, the images change to coincide with the study being displayed, and other views that relate to the active visit change). Additionally, views on other pages may be updated as well. For example, the CR view (4th tab) remains consistent with the Pulmonologist view (first tab) which contains information relevant to the Oct. 3, 1999 visit after the change. However, as noted above, some display elements do not change information (e.g., demographic information may not change (and should not change in the illustrated example) between visits for the same person).

The functionality of creating an active component that follows a Context Variable is configurable. A component can be configured to track a Context Variable or to remain set to a static view. For example, the CR Study viewer above tracks the active visit. The same component can be configured to display only the most recent CR Study. Therefore, when the user changes the active visit, the most recent CR study will always be displayed.

Preferably, the structure of the Context Variables is also stored in a hierarchical structure (e.g., a structure similar to the Patient description language). The Context Structure contains a variable for each branch in the patient-tree structure. By doing this, the active portion of the patient information can be tracked.

Figure 6:
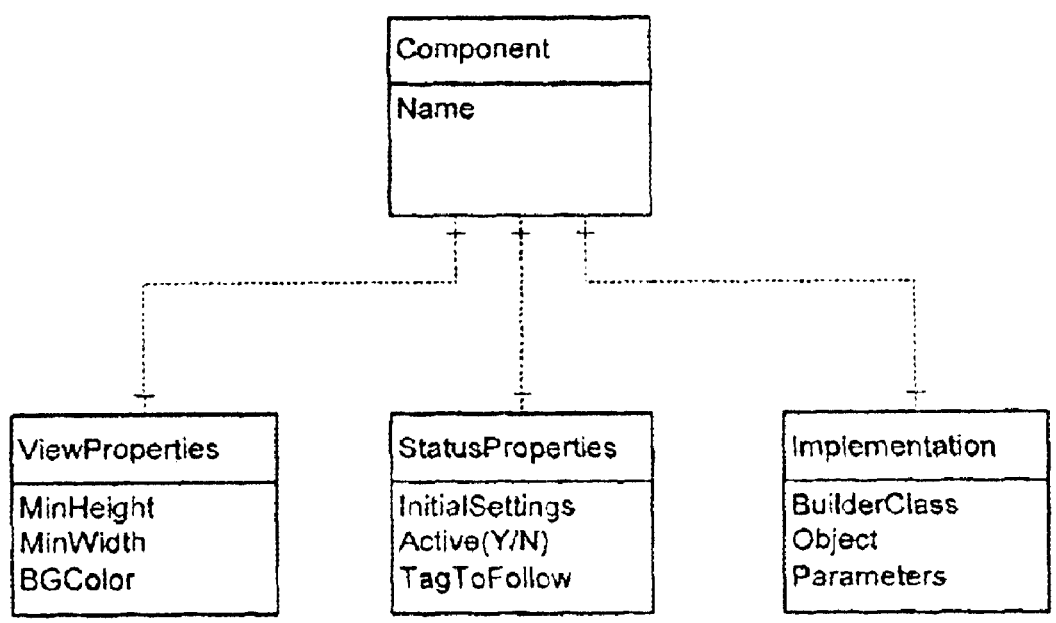
FIG. 6 is an entity-relationship diagram representing relationships between various layout components within the system.

As shown in an exemplary entity-relationship diagram of FIG. 6, a component includes three types of information stored in the form of properties: View, Status and Implementation properties. Generally, this component model is applicable to either (1) an implementation that stores data independently from the components (as described above) or (2) an implementation that stores data with the components (e.g., by storing the configuration of a Java Bean within the Bean itself).

View properties suggest how the component should be displayed, but a layoutController, a driving component in the Patient Context component, controls how the component will look in its final presentation. As illustrated in FIG. 6, exemplary properties include: (1) the minimum height and width, MinHeight and MinWidth, respectively, in which the component should be displayed and (2) the optimal background color, BGColor.

Similarly, the StatusProperties of components describe how the component should behave in the context of the application. Exemplary properties refer to initial setting specifying how the component will be invoked. The status variables are variables that correspond to element tags (e.g., visit in FIG. 5A) of the Patient description language. Numeric value may include pre-defined meanings (e.g., 0=most recent, 1=most recent previous, 2=second most recent previous, etc.). Other status properties describe how the component behaves as the user works. That behavior includes changing the state of the overall system, e.g., by selecting a new active visit from a VisitList Component.

The Active property is a boolean expression that describes if the component should change with the active status or if it should remain at its initial settings throughout the duration of the session. A "Yes" status indicates that the component should change to follow the settings of other components. A "No" status indicates that the component should remain at its initial settings.

The TagToFollow property indicates the lowest level tag in the status hierarchy that should be used to modify the component's state. For example, the CRImageViewer tracks the status tag CRStudy. Whenever the user selects a different CRStudy (i.e., the status of CRStudy changes) the CRImageViewer will change to track the value of CRStudy.

The Implementation property describes the actual implementation of the component. It allows the system to create a wrapper to invoke the actual run-time component with the proper parameters. The BuilderClass property describes the type of the component. As described above, numerous types (e.g., JavaClasses) of implementation technologies can be used according to the present invention. The Path property describes the location of the software to be executed. The Parameter property provides any additional start-up parameters that are not specified in StatusProperties.InitialSettings variables (e.g., user identification and passwords).

Although other structures or formats could be used to describe the properties described above with reference to FIG. 6, in the preferred embodiment, the properties are described using an XML-based grammar. In FIG. 7, the view properties and status properties of FIG. 6 are specified with exemplary values for a Study List Component that displays information about CR and Derm Studies. The minimum height and width of the components are specified as 180 and 320 pixels, respectively. The background color is specified as black. Visit and study both utilize the most recent values (i.e., the most recent visit and study, respectively). Also, the component is active so that it tracks changes in other components by following the visit variable.

The highest level of the description language contains identifying information about the patient. It allows demographics and visit information to be expandable therefrom. The patient description language is essentially taken from the DICOM view of the 'real world'. It connects patient information with visits. Visits are used to group care episodes into meaningful chunks, especially in a hospital setting. In an outpatient or clinic setting a more useful grouping might be Diagnostic Code or some other piece of information that groups patient information into episodes of care. For example, it would group information related to a broken leg together and logically separate that information from information about a heart condition.

This information could also be stored in the format of another standard—like the HL7 RIM model. However, this information does not need to be structured in the same format as it is structured in the database as long as its structure supports the task.

Context Variables within the application are maintained for points where the patient structure tree branches. If a branch of the tree is maintained for each type of study (e.g., CRStudy, DermStudy, CTStudy), context information can be maintained for these variables since it is known which study is active at any given time. Visit variables contain information about visits (e.g., what group studies a visit corresponds to and what medications were utilized or prescribed).

CRStudy contains only CR Modality information. It contains some general information about the study and one or more Series elements. The actual images are contained at the Series level.

The format of the ECGStudy element parallels that of the CRStudy. Again, the highest level contains general information about the study, and there are one or more Series elements. The images are contained at the Series level.

Figure 8:
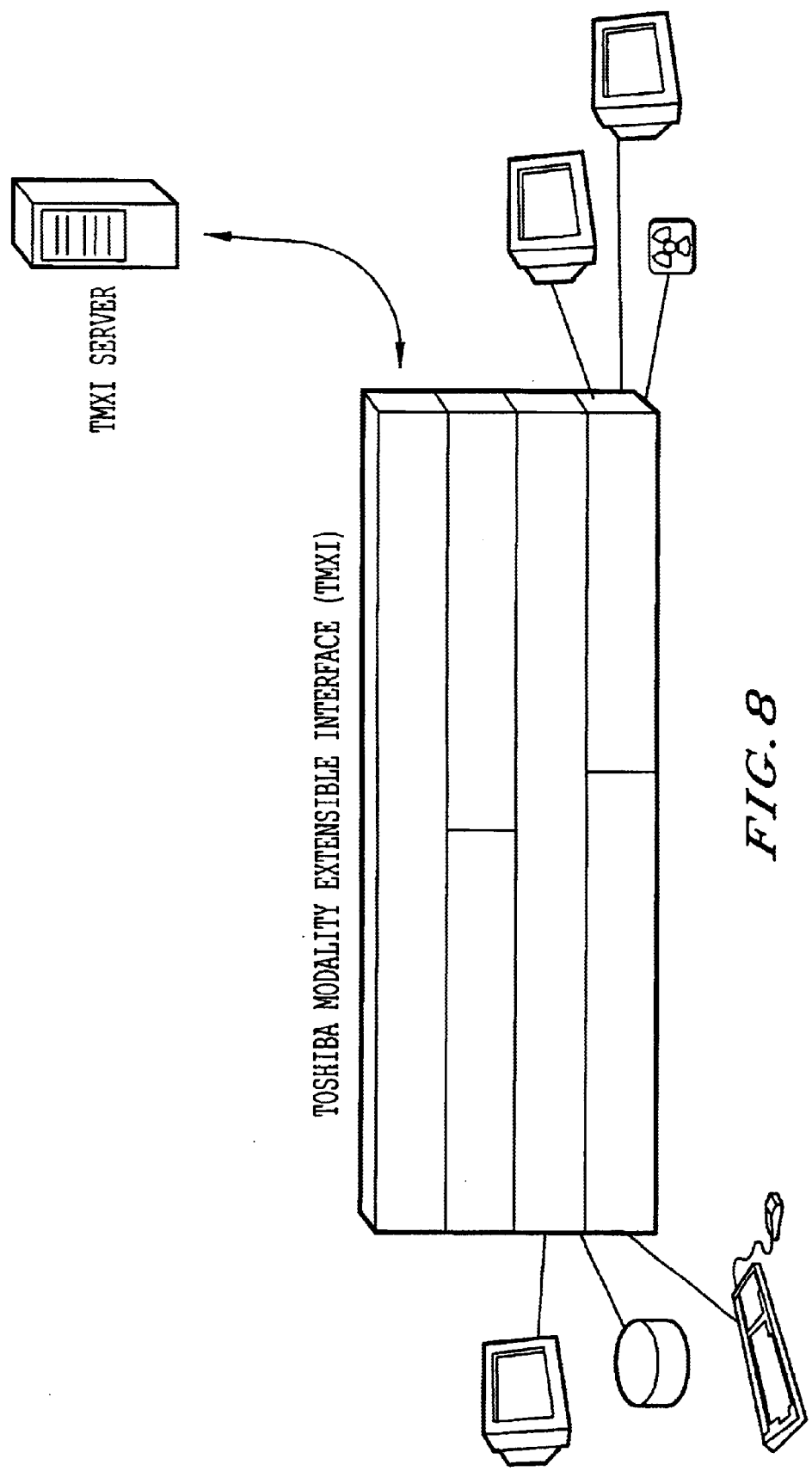
FIG. 8 is a block diagram of a division of interfaces that enables hardware-specific or modality-specific components from hardware- and modaility-independent components.

In order to further facilitate re-use, in one embodiment, components that are modality specific are separated from those which are modality independent. Modality specific components will generally be those which control physical hardware processes unique to a given modality. At the "bottom" interface these components will control transducers or digital I/O interfaces that are necessary for controlling the generation of radiation, mechanical operation or other hardware activities. At the "top" these components should be designed to provide a common interface to the next layer of abstraction that is independent of any modality. Modality independent software may include DICOM communications and formatting software components, file management components, systems management and maintenance tools, DICOM modality worklist components, DICOM MPPS components, etc (see FIG. 8).

Such an implementation allows for more general purpose definition of DSUIs through "layouts" for user-interfaces for modalities that are customized to individual needs (e.g., hospital sites or individual medical professionals (e.g., doctors, nurses and medical administrators)). The design, creation and modification of custom layouts may be accomplished by end-users working with a layout editor tool. New layouts, or management/maintenance layout may further be downloaded using standard web communications protocols. Maintenance layouts may access specialized components that are not accessible to end-users layouts.

A single page of a layout is described by a hierarchical structure that contains a recursive nesting of panels. This enables a layout to become a sub-layout transparently to the layout, simply by referencing the layout in a "higher level" layout. At each level the panel has display properties to help control and reference the layout. Exemplary properties are illustrated in FIG. 10B.

The Title property is an optional property that may be used to associate a name to be displayed as part of a particular layout. The Model property is utilized for determining whether the area assigned to the component will be sub-divided. Exemplary types of Model parameters include:

FULL: the component will take up the full panel;
HHALF (horizontal half): The panel will be divided horizontally into two panels;
VHALF (vertical half): The panel will be divided vertically into two panels;
HTHIRD (horizontal third): The panel will be divided horizontally into three panels; and
VTHIRD (vertical third): The panel will be divided vertically into three panels.

However, as would be appreciated, additional divisions are possible and encompassed within the scope of the invention.

The Location property can include Directional coordinates such as North, South, East, and West. These indicate which panels are being referenced within the properties.

As shown in FIGS. 9A–9D, various panels (which may incorporate sub-panels) can be specified for various functions. The Full model may be used for image display. The Horizontal Half model may be used to display two comparison images. The Vertical Third model may be used to display a study list and two images.

If, however, four images were to be displayed on the screen as shown in FIG. 9D, no one component, of the components described above, can be used to provide that functionality directly. Accordingly, the components are used hierarchically to simulate the desired behavior. For example, a Horizontal Half Model where each of the panels contained a Vertical Half Model produces the desired result. An exemplary XML-based description for achieving the four panel display of FIG. 9D is illustrated in FIG. 10A. Such a layout can then be stored in a library of layouts for re-use later.

Figure 11:
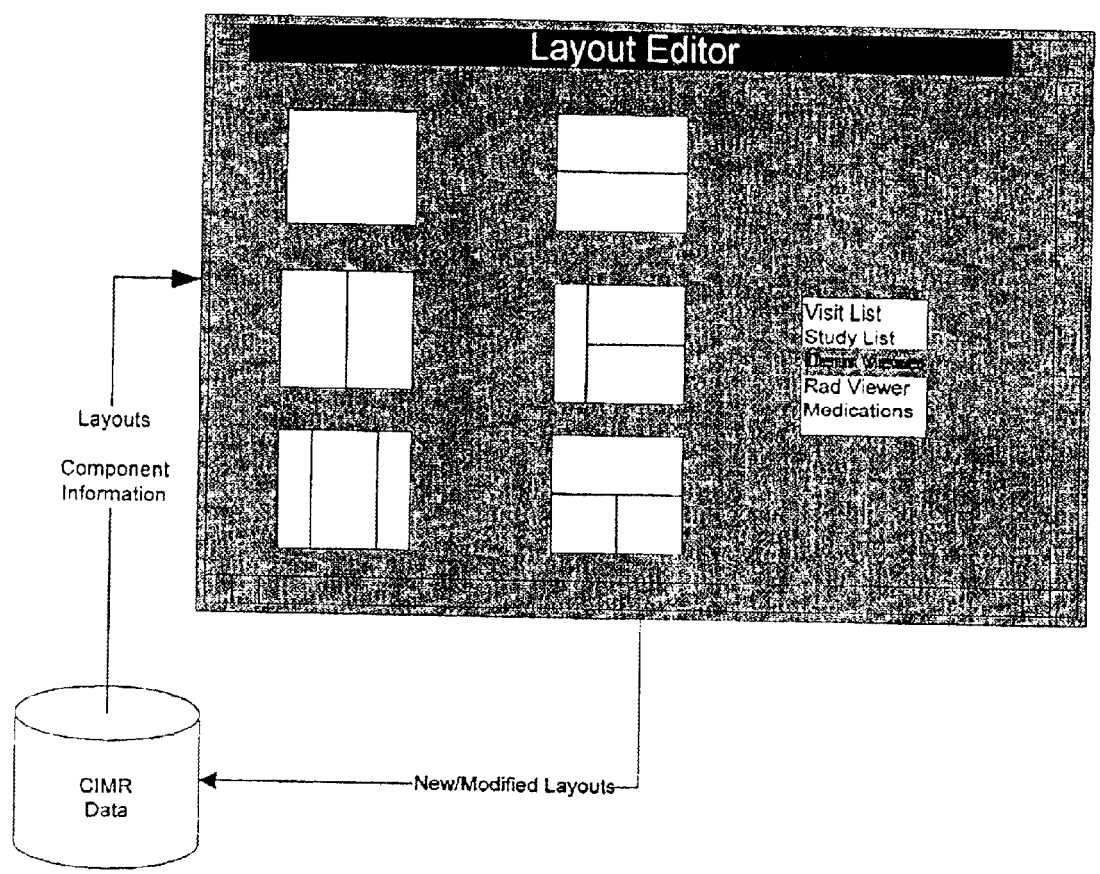
FIG. 11 is an exemplary layout editor for defining hierarchies of panels.

Rather than create all new layouts by hand, it is preferable to utilize a layout editor, such as is shown in FIG. 11. The Layout Editor uses component information (e.g., stored in a local data source). Preferably, the component information describing the layout is stored in an XML structure as described above. Since panels can include panels as components, the layouts can be created rather quickly. An exemplary grammar for describing layouts (either generated by hand or through the layout editor) is illustrated in FIG. 12. Such a grammar describes the elements of a layout and in what order the elements are to appear (including any repetitions or optional elements).

Although the above-description has focused on an implementation using applets as illustrated in FIG. 2, other implementation technology not based on applets is also possible, and indeed is preferable. One drawback in utilizing applets is that applets cannot share their display screens with other software modules (e.g., ActiveX Controls, other Applets). This restriction runs counter to allowing the integration of third-party software into a single display environment.

Figure 13:
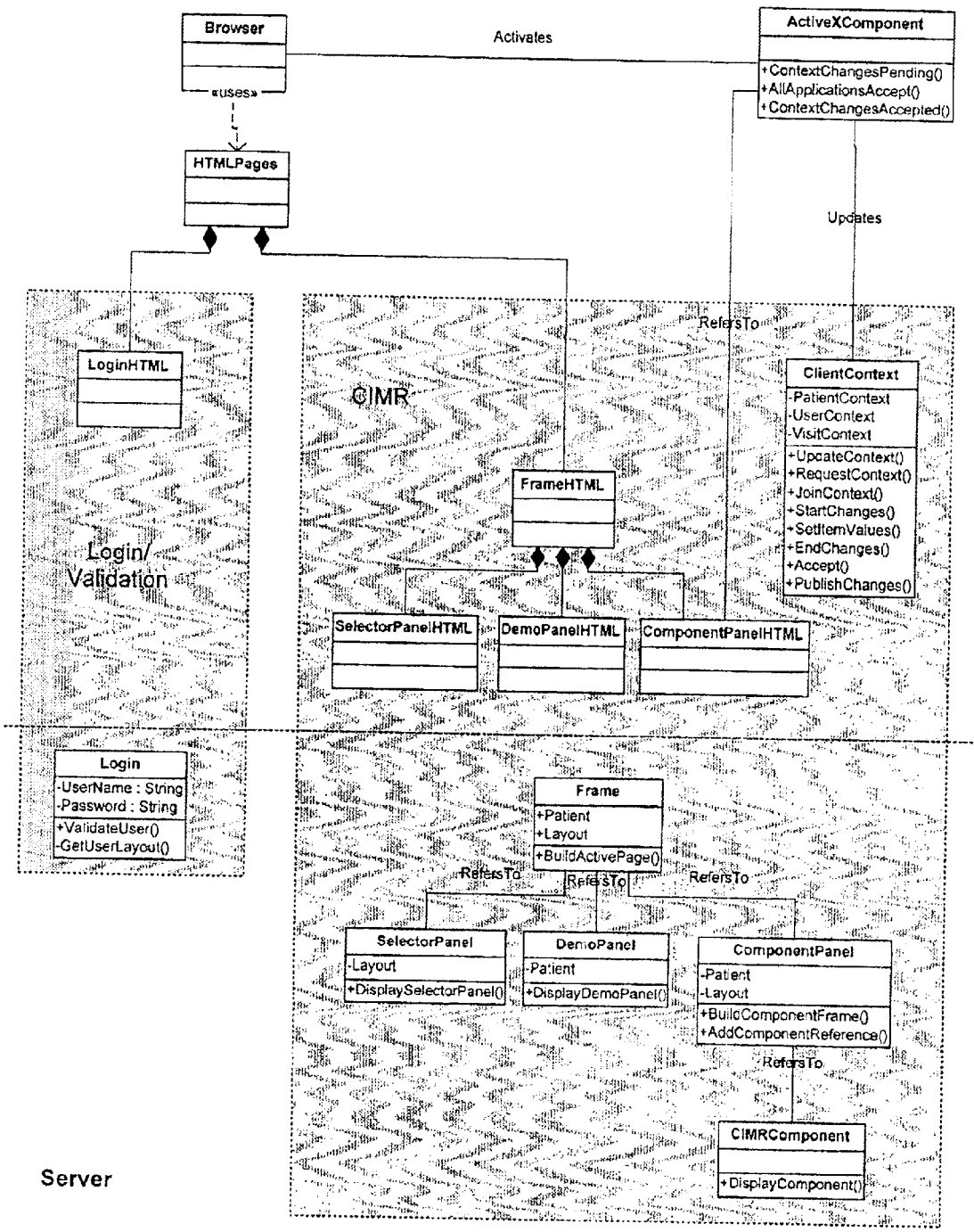
FIG. 13 is an entity-relationship diagram for implementing the DSUIs of the present invention without using applets.

A first alternate implementation technique, not based on applets, includes a native windows application. The basic structure of the software would remain the same but the container would be changed from an applet to an application. A second alternate implementation technique, not based on applets, includes a thin client, as shown in FIG. 13. It is this alternate implementation technique that is described in greater detail below. Such a technique may utilize servlets, DHTML, CSS and COM.

Both such implementations may be extended to allow applications, including third-party software, to share a common context (e.g., information about an active patient or visit) that can change. Applications written to expressly handle such sharing messages are referred to hereinafter as "context-aware" applications. Integrated sharing, however, is hindered by applications that were not written to expect events or communications from sources other than input devices (e.g., the keyboard and mouse). Such applications are referred to hereinafter as "context-unaware" applications. For such context-unaware applications, sharing can be achieved by utilizing a context or display manager (CDM) that terminates the context-unaware applications and restarts them with the appropriate parameters. One messaging standard that can be used for context-aware applications is CCOW, as discussed above, and tools (e.g., from Sentillion) facilitate creation of such CCOW-based applications. The Sentillion development package contains:

Context Participant: A DLL that can be embedded within an application that implements most of the context participant application behaviors defined in the CCOW standard.

Context Manager: A development-only version of a Context Manager. The Context Manager enables clinical applications to be synchronized around a common clinical context. The Context Manager runs as a server process and acts as the broker for CCOW messages. Herein, it is referred to as the Clinical Context.

Returning to FIG. 13, FIG. 13 illustrates a conceptual model using a thin client architecture that distributes services between a client (e.g., using a browser as a client interface) and at least one server. In a first embodiment, a series of HTML pages are used, including a first set of pages that interact with a server (e.g., using a Login Servlet) to validate the user and determine the patient. The second set of pages includes plural frames (e.g., 3 frames). An exemplary page generated according to the present invention was discussed above with reference to FIG. 3. Each of the frames interacts with the server (using servlets). In such an environment, context information is kept within the client and is based on a messaging protocol (e.g., CCOW). The client context is maintained within a context server on the client, and the components interact directly with the client context.

Preferably, the thin-client is constructed in a two-phase initialization process. The first phase of the initialization builds a layout (e.g., using an HTML page) of the components to be used in the DSUI, and in the second phase, the client activates the components thereof. During operation, a user can interact with each of the control component (e.g., by selecting tabs from the tab bar of FIG. 3). This changes the page of information that is being displayed. The user can also interact directly with components. These components communicate directly with the context manager or context object.

Figure 14:
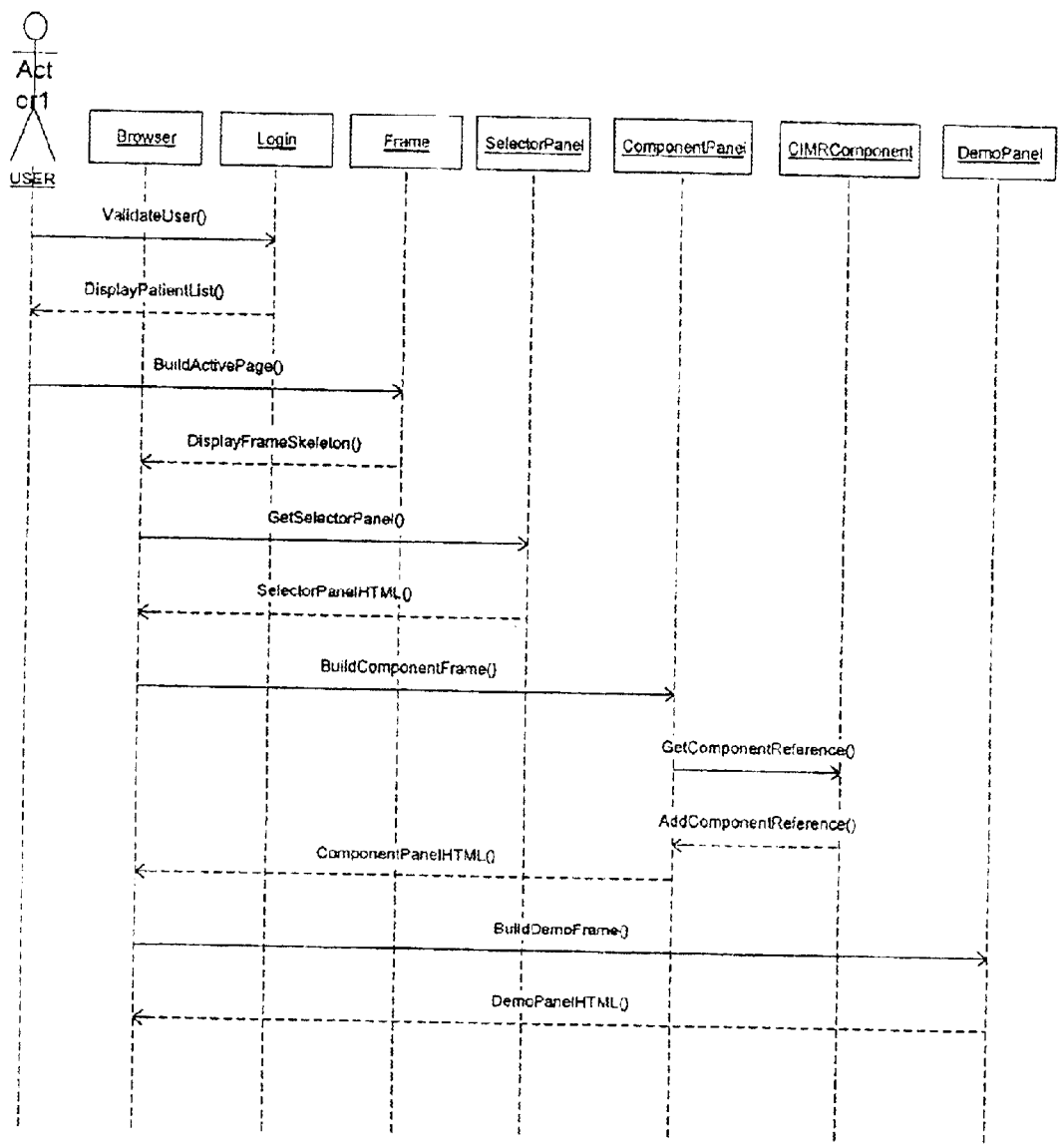
FIG. 14 is a message sequence diagram illustrating an initialization of a thin client implementation of the present invention.

FIG. 14 illustrates the sequence diagram for the construction of the component page. Most of the activity takes place on the server. The client interface is the only software component on the client that need be active in the initial building of the page. The client interface requests login information (e.g., (1) authentication code or (2) user id and password) from a user. The server (e.g., using a login servlet) authenticates the user and returns a patient selection list and a DisplayLayout (that refers to structured display list file (e.g., an XML file) on the server). The user selects a patient, and the ActivePatient reference and display layout are sent to the server (e.g., a Frame Servlet). The server uses the ActivePatient reference to construct patient information in the patient description language. The server then creates page layout controls (e.g., a set of frames) that correspond with the display layout and the ActivePatient and returns the page skeleton to the client interface. Page layout controls of the page skeleton include references to the servlets that will fill in the page layout control areas along with the necessary parameter information.

In the exemplary embodiment of FIG. 14, three frames (i.e., a selector panel frame, a component panel frame, and a demo panel frame) are used as page layout controls. The SelectorPanel Frame includes a reference to the SelectorPanel Servlet with a display layout parameter. The SelectorPanel Servlet sends back a control layout (labeled SelectorPanelHTML) that produces the tab bar at the top of the interface. Preferably the tab bar is implemented in DHTML so all visual changes to the tab bar take place on the client (e.g., the tabs changing color when the cursor moves over them).

The component panel frame includes a reference to the ComponentPanel Servlet. The client interface activates the ComponentPanel Servlet reference with the ActivePatient and display layout information. The ComponentPanel further subdivides its display area to correspond with a specified layout (e.g., divided in vertical or horizontal halves, or vertical or horizontal thirds). The ComponentPanel Servlet then inserts a fully qualified reference to the component (e.g., the ActiveX component) in each of the frames that it has created. This control layout (labeled ComponentPanelHTML) is returned to the client interface for display.

The DemoPanel Frame includes a reference to the DemoPanel Servlet. The client interface activates the DemoPanel Servlet reference with the ActivePatient parameter. The DemoPanel Servlet creates a patient demographic display from the patient description language structure.

The three servlets process independently and produce display pages (e.g., HTML) as an output. It is very simple to change the look of thin-client by changing the display pages that are output. For example, the tab panel can be moved to the bottom, font and background colors can be easily changed, and frame and font sizes can be modified by simply changing the style sheet.

Figure 15:
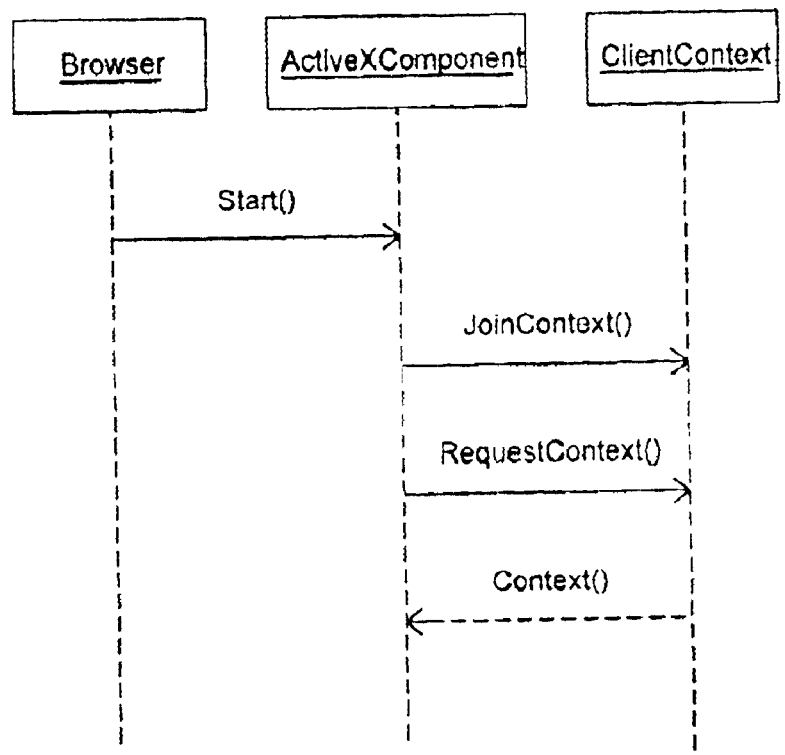
FIG. 15 is a message sequence diagram illustrating the registering of components to receive context information.

FIG. 15 illustrates a sequence diagram that shows the second part of the activation phase. In this phase, the client interface activates the components with the parameters that are specified in their page layout references. The context-aware components then join the common context. This enables components to receive later context update messages and request the current context. The context is returned as a series of name value pairs.

Figure 16:
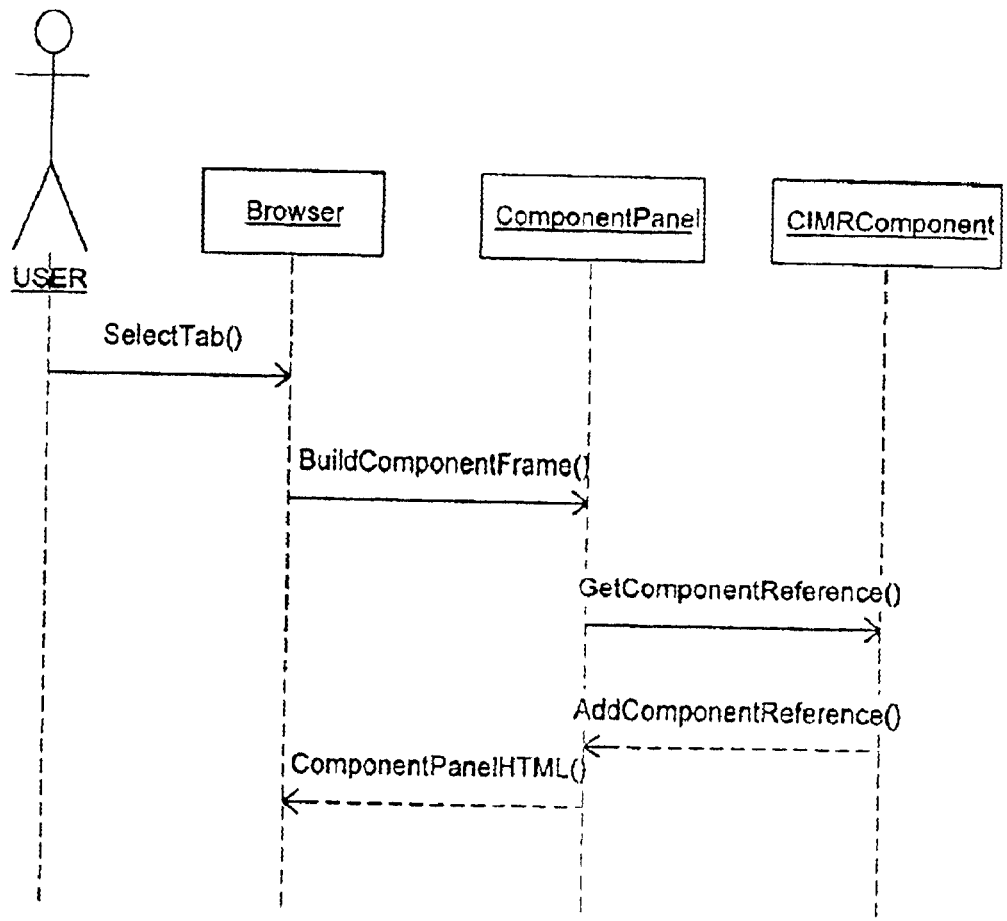
FIG. 16 is a message sequence diagram illustrating the building of a component interface.
Figure 17:
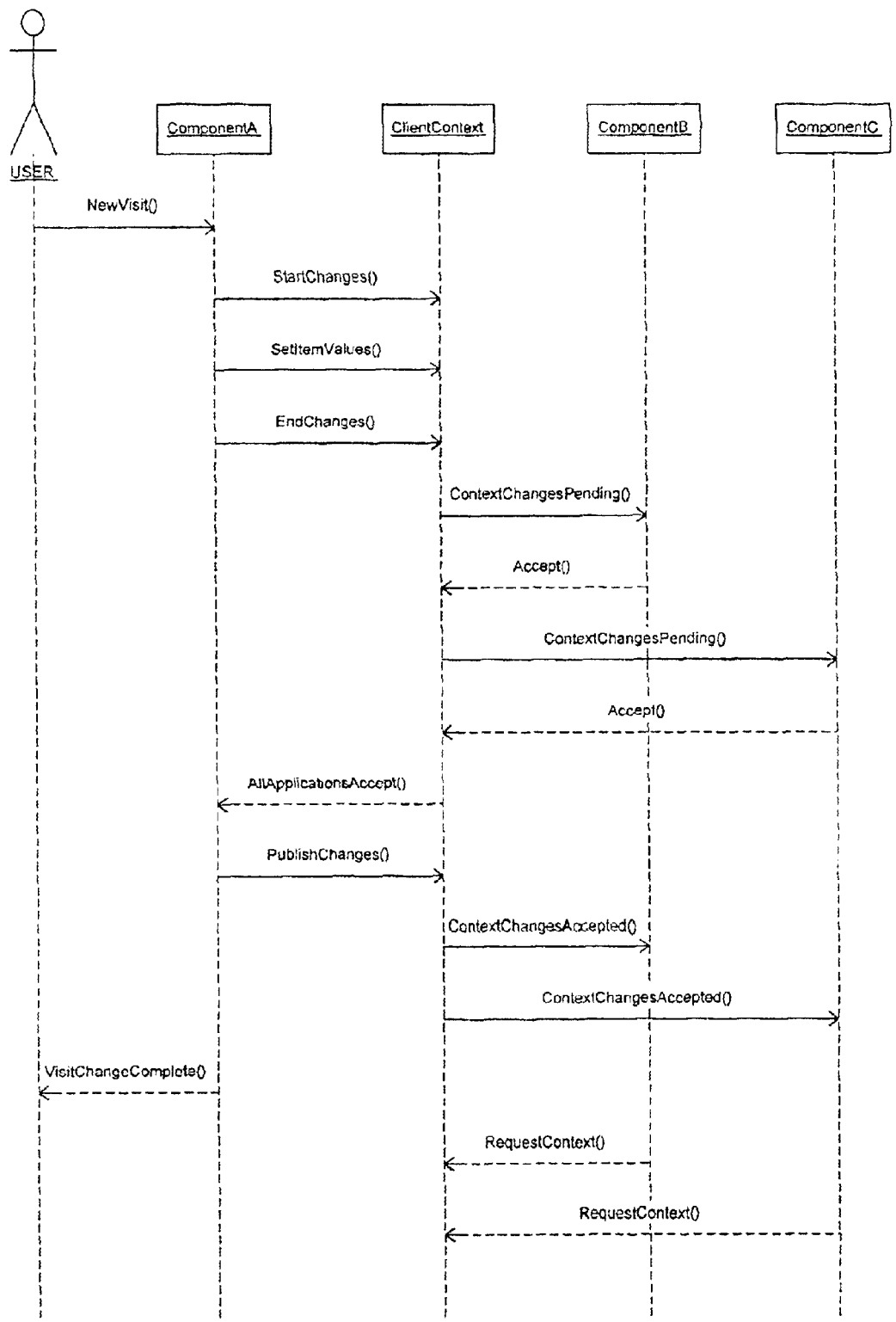
FIG. 17 is a message sequence diagram illustrating the process of changing context information.

Returning to the user interface of FIG. 3, the user can change the display page (e.g., by selecting a tab from the tab bar) or interact directly with an application that is being displayed in one of the component areas frames of the ComponentPanel Frame. FIGS. 16 and 17 illustrate the sequence of steps used in the changes and interactions, respectively.

In one embodiment of the present invention, the SelectorPanel Servlet and the SelectorPanelFrame create the initial display for the tab bar in the CIMR display. In such an embodiment, the frame contains dynamic control (e.g., DHTML) and all cursor movement and display update occurs within the display through scripts (e.g., through JavaScript-based DHTML). In one embodiment, each of the tabs is a "submit button" that, when selected by the user, sends a message to a Servlet. In the initialization, SelectorPanel Servlet determines which page of the DisplayLayout corresponds with each tab. The identification for the DisplayLayout page is inserted into the dynamic control reference that corresponds with the "submit button" related to the tab display. Thus, the dynamic control takes care of changes in the display (e.g., highlighting the tab when the cursor moves over it, making the selected tab appear to be displayed in the front of the other tabs) and the SelectorPanel display corresponds directly with the ComponentPanel Servlet.

The client interface activates the ComponentPanel Servlet reference with information that is contained within the "submit button" reference. As it did in the initialization, the control layout further subdivides its display area to correspond with the active page (e.g., divided in vertical or horizontal halves, vertical or horizontal thirds). The ComponentPanel Servlet then inserts a fully qualified reference to the component in each of the controls that it has created. This control layout is returned to the client interface for display (e.g., as an HTML page).

Once the control layout is returned to the Browser, the client interface activates the related components in the same manner that is described in FIG. 15. Each of the components joins the active context and gets the active context from the Clinical Context object.

The second type of user interaction involves the user interacting directly with a component. The component, not the user, interacts with the shared environment by sending and receiving context information from the context manager or context object. In one embodiment, the context-changing interaction occurs completely on the client without communication with the server side. In an alternate embodiment, context-changing may occur with communication to the server (e.g., to record when components were interacted with).

FIG. 17 illustrates a sequence diagram for a successful context change using a context manager/object. The sequence begins when a user selects a new context variable in a component. In this case, the context variable is the visit. The context-aware component then begins a protocol to insure that only one application can change context simultaneously and that no changes are lost. The context-aware component sends a StartChanges message to the context manager/object. This locks out other applications from beginning a context change and gives the initiating application a blank context area to begin work. The application then sends a series of messages to set the new context variables followed by the EndChanges message. When the EndChanges message is received, the context manager/object is free to accept other requests for message changes. The context manager/object then sends a message to all other applications that are members of the context (i.e., that have joined the context) that there is a new context pending. In the exemplary embodiment of FIG. 17, all applications accept the new context (although other responses are possible). If all of the applications accept the new context, the context manager/object sends a message to the initiating component indicating that all applications accepted. The initiating component sends a message to the clinical context to replace the current context with the accepted context. The clinical context sends out to all members of the context that the new context is now active. The applications then request the new context and make the required changes.

It is also possible that not all components accept, so other responses, as described below, are also valid. Exemplary responses (that are not "Accept") include:

Accept-Conditional: It is in the midst of a task that might cause work to be lost if the user does not complete the task; if changes are published it is willing to terminate the task, accept the context data changes and change its internal state accordingly. If changes are subsequently published, an application can defer changing its internal state until some time in the future (for example, when it regains the focus for user-inputs). However, it must offer a visual cue that indicates it is not in synchrony with the new context. For example, it might blank out its data display or minimize itself.

Terminated: The application has terminated without first informing the Clinical Context. This will not affect the context change, and the application is removed from the context.

Busy: The context manager has determined that the application is still running but is unable to answer (e.g., the application is single-threaded and has a modal dialog open). When an application is busy, the initiating components are provided with a succinct but informative descriptions (including names) of any applications that are busy. This information is provided by the Clinical Context on behalf of these applications, as they are unable to do so for themselves. The initiating application can choose to display an informational message to the user.

To avoid information loss, the context changer utilizes a token in order to make any changes. Also, the context participant that is making changes must be able to deal with busy participants. The application must include either code to make a decision regarding whether the context change should proceed or code to prompt the user as to whether or not to proceed with a context change. Although conceptually it would be preferable to not involve a user in a system decision (e.g., the display program is busy do you still want to change the active visit), code to make the decision automatically may not be practical.

Clearly, numerous modifications and variations of the present invention are possible in light of the above teachings. It is therefore to be understood that, within the scope of the appended claims, the invention may be practiced otherwise than as specifically described herein.

What is claimed is:

1. A computer program product, comprising:
   a computer storage medium and a computer program code mechanism embedded in the computer storage medium for causing plural independent executable components to form an integrated display of medical images and data on a medical workstation, the computer program code mechanism comprising:

a first computer code device configured to generate on a medical workstation an integrated display window to be shared by the plural independent executable components displaying medical images and data, the integrated display window comprising a plurality of panels, each of the plural independent executable components displaying on one of the plurality of panels;

a second computer code device configured to specify relative locations for each of the plurality of panels within the integrated display window;

a third computer code device configured to launch said plural independent executable components using the specified relative locations;

a fourth computer code device associated with a first component of the plural independent executable components configured to receive notifications about changes in data displayed by a second component of the plural independent executable components; and a fifth computer code device in the second component configured to send, to the first component, notifications about changes in the data displayed by the second component, wherein at least one of the plural independent executable components comprises a read-only component that is not configured to receive the notifications, and wherein the fourth computer code device comprises a sixth computer code device configured to restart the read-only component with new run-time arguments when the fourth computer code device receives the notifications.

2. The computer program product as claimed in claim 1, wherein the third computer code device further comprises a fifth computer code device configured to pass corresponding run-time arguments to the plural independent executable components.

3. The computer program product as claimed in claim 1, wherein the fourth computer code device is embedded within the first component.

4. The computer program product as claimed in claim 1, wherein the notifications comprise Clinical Context Object Working Group (CCOW) messages.

5. The computer program product as claimed in claim 1, wherein the second computer code device further comprises a sixth computer code device configured to parse an eXtended Markup Language (XML) Specification specifying the relative locations for each of the plural independent executable components.

6. The computer program product as claimed in claim 5, wherein the sixth computer code device further comprises a seventh computer code device configured to parse absolute size measurements.

7. The computer program product as claimed in claim 5, wherein the sixth computer code device further comprises a seventh computer code device configured to parse window pane specifications.

8. The computer program product as claimed in claim 1, wherein the second computer code device comprises a sixth computer code device configured to receive doctor input to customize the relative locations for each of the plural independent executable components within the integrated display window.

9. The computer program product as claimed in claim 1, wherein the data displayed by a second component is displayed in a first format and retrieved in a second format, wherein the first and second formats are different.

10. The computer program product as claimed in claim 9, wherein at least one of the first and second formats comprise an XML-based data format.

11. The computer program product as claimed in claim 1, wherein the data comprises at least one of patient visit, study and series data.

12. The computer program product as claimed in claim 11, wherein the data comprises data in an XML-based data format.

13. The computer program product as claimed in claim 1, wherein the computer program code mechanism is platform-independent.

14. A medical workstation, comprising:

means for generating on a medical workstation an integrated display window to be shared by plural independent executable components displaying medical images and data, the integrated display window comprising a plurality of panels, each of the plural independent executable components displaying on one of the plurality of panels;

means for specifying relative locations for each of the plurality of panels within the integrated display window;

means for launching said plural independent executable components using the specified relative locations;

means, associated with a first component of the plural independent executable components, for receiving notifications about changes in data displayed by a second component of the plural independent executable components; and means, in the second component, for sending to the first component, notifications about changes in the data displayed by the second component, wherein at least one of the plural independent executable components comprises a read-only component that is not configured to receive the notifications, and wherein the means for receiving comprises means for restarting the read-only component with new run-time arguments when the means for receiving receives the notifications.

15. The medical workstation as claimed in claim 14, further comprising means for converting the data from a first format used for storage to a second format used for display.

16. The medical workstation as claimed in claim 14, further comprising means for customizing a set of components used for display of the data.

17. A method of operating a medical workstation comprising:

generating on a medical workstation an integrated display window to be shared by plural independent executable components displaying medical images and data, the integrated display window comprising a plurality of panels, each of the plural independent executable components displaying on one of the plurality of panels;

specifying relative locations for each of the plurality of panels within the integrated display window;

launching said plural independent executable components using the specified relative locations;

sending, from a second component of the plural independent executable components to a first component of the plural independent executable components, notifications about changes in the data displayed by the second component; and receiving, in the first component, notifications about changes in data displayed by the second component, wherein at least one of the plural independent executable components comprises a read-only component that is not configured to receive the notifications; and wherein the receiving step comprises restarting the read-only component with new run-time arguments when the notifications are received.

18. The method as claimed in claim 17, further comprising converting the data from a first format used for storage to a second format used for display.

19. The method as claimed in claim 18, further comprising customizing a set of components used for display of the data.

20. The method as claimed in claim 18, further comprising customizing, by a medical professional, a set of components used for display of medical data.

21. A computer program product, comprising:

a computer storage medium and a platform-independent computer program code mechanism embedded in the computer storage medium for causing plural independent executable components to form an integrated display of medical images and data on a medical workstation, the computer program code mechanism comprising:

a first computer code device configured to generate on a medical workstation an integrated display window to be shared by the plural independent executable components displaying medical images and data;

a second computer code device configured to specify relative locations for each of the plural independent executable components within the integrated display window;

a third computer code device configured to launch said plural independent executable components using the specified relative locations;

a fourth computer code device associated with a first component of the plural independent executable components configured to receive notifications about changes in data displayed by a second component of the plural independent executable components; and a fifth computer code device in the second component configured to send, to the first component, notifications about changes in the data displayed by the second component, wherein at least one of the plural independent executable components comprises a read-only component that is not configured to receive the notifications; and wherein the fourth computer code device comprises a sixth computer code device configured to restart the read-only component with new run-time arguments when the fourth computer code device receives the notifications.

* * * * *